US010709680B2

(12) United States Patent
Smith et al.

(10) Patent No.: US 10,709,680 B2
(45) Date of Patent: *Jul. 14, 2020

(54) METHODS FOR TREATING DRY EYE

(71) Applicant: Physicians Recommended Nutriceuticals, LLC, Blue Bell, PA (US)

(72) Inventors: S. Gregory Smith, Yorklyn (DE); Michael B. Gross, Plymouth Meeting, PA (US); Olav E. Sandnes, Mt. Bethel, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/910,661

(22) Filed: Mar. 2, 2018

(65) Prior Publication Data

US 2018/0214407 A1  Aug. 2, 2018

Related U.S. Application Data

(63) Continuation-in-part of application No. 15/197,212, filed on Jun. 29, 2016, now abandoned, which is a continuation-in-part of application No. 13/815,599, filed on Mar. 12, 2013, now Pat. No. 9,381,183, which is a continuation-in-part of application No. 13/507,673, filed on Jul. 18, 2012, now Pat. No. 9,115,078.

(60) Provisional application No. 61/572,574, filed on Jul. 18, 2011.

(51) Int. Cl.
| | | |
|---|---|---|
| *A61K 31/202* | (2006.01) | |
| *A61P 27/04* | (2006.01) | |
| *A61K 31/593* | (2006.01) | |
| *A61K 31/215* | (2006.01) | |
| *A61K 31/232* | (2006.01) | |

(52) U.S. Cl.
CPC .......... *A61K 31/202* (2013.01); *A61K 31/215* (2013.01); *A61K 31/232* (2013.01); *A61K 31/593* (2013.01); *A61P 27/04* (2018.01)

(58) Field of Classification Search
CPC .. A61K 31/202; A61K 31/215; A61K 31/232; A61K 9/0053; A61P 3/06; A61P 27/04
See application file for complete search history.

(56) References Cited

U.S. PATENT DOCUMENTS

| | | | |
|---|---|---|---|
| 6,353,022 B1 | 3/2002 | Schneider et al. | |
| 6,506,412 B2 | 1/2003 | Troyer et al. | |
| 6,566,398 B1 | 5/2003 | Ueno | |
| 6,649,195 B1 | 11/2003 | Gorsek | |
| 7,417,071 B2 | 8/2008 | Gandhi | |
| 9,115,078 B2 * | 8/2015 | Smith | C07C 69/587 |
| 9,314,445 B2 | 4/2016 | Georgiou | |
| 9,381,183 B2 * | 7/2016 | Smith | A61K 31/202 |
| 9,675,575 B2 * | 6/2017 | Sandnes | A61K 31/202 |
| 10,034,849 B2 * | 7/2018 | Sandnes | A61K 35/618 |
| 2004/0048926 A1 | 3/2004 | Hoffman et al. | |
| 2004/0076695 A1 | 4/2004 | Gilbard | |
| 2005/0147648 A1 | 7/2005 | Gierhart | |
| 2006/0127505 A1 | 6/2006 | Haines et al. | |
| 2006/0135610 A1 * | 6/2006 | Bortz | A61K 31/202 514/548 |
| 2007/0032546 A1 * | 2/2007 | Almarsson | A61K 31/12 514/494 |
| 2007/0141138 A1 * | 6/2007 | Feuerstein | A61K 9/48 424/451 |
| 2007/0141170 A1 | 6/2007 | Lang | |
| 2007/0265341 A1 | 11/2007 | Dana et al. | |
| 2008/0260859 A1 | 10/2008 | Claherz et al. | |
| 2008/0292681 A1 * | 11/2008 | Domingo Pedrol | A61K 31/202 424/439 |
| 2009/0136445 A1 | 5/2009 | Wong et al. | |
| 2009/0182049 A1 * | 7/2009 | Opheim | A61K 31/202 514/560 |
| 2009/0226547 A1 | 9/2009 | Gilbard et al. | |
| 2010/0028459 A1 | 2/2010 | Kis | |
| 2010/0048705 A1 | 2/2010 | Smith et al. | |
| 2010/0068298 A1 | 3/2010 | Kis | |
| 2010/0093648 A1 | 4/2010 | Cruz | |
| 2010/0330171 A1 | 12/2010 | Gilbard et al. | |

(Continued)

OTHER PUBLICATIONS

Roncone et al., "Essential fatty acids for dry eye: A review," Cont. Lens Anterior Eye Apr. 2010;33(2):49-54. PMID: 20031476. (Year: 2010).*
Basic & Clinical Pharmacology, 7th Ed. By Katzung (Ed.), Simon & Schuster Co. (Stamford, Conn.). (Year: 1998).*
Wojtowicz et al., Pilot, Prospective, Randomized, Double-masked, Placebo-controlled Clinical Trial of an Omega-3 Supplement for Dry Eye, Cornea, Mar. 2011, Cornea, vol. 30, No. 3, pp. 308-314.
Ascenta, Fish Oil Triglycerides vs Ethyl Esters: A comparative review of absorption, stability and safety concerns, 2008, www.ascentahealth.com/print/373, pp. 1-9.

(Continued)

*Primary Examiner* — Theodore R. West
(74) *Attorney, Agent, or Firm* — Pierce IP Law, PLLC

(57) ABSTRACT

This invention relates to methods for improving the quality of the meibum composition of the meibomian glands to enhance or improve the lipid layer of the tear and increase tear breakup time by way of elevating the omega-3 index in patients suffering from symptoms of dry eye, posterior blepharitis, and/or meibomian gland dysfunction. The methods comprise administering a supplementation of omega-3 fatty acids to a patient having an inflamed meibomian gland so as to facilitate an increase in the amount of omega-3's acting as an anti-inflammatory and, respectively, decrease the amount of omega-6's (arachidonic acid) acting as an inflammatory in the composition of the meibum, thereby normalizing the lipid layer of the tear and effectively reducing the associated symptoms. In certain embodiments, the supplementation of omega-3's comprises the esterified or re-esterified triglyceride form.

20 Claims, No Drawings

(56) References Cited

U.S. PATENT DOCUMENTS

| | | |
|---|---|---|
| 2011/0111055 A1 | 5/2011 | Lang |
| 2012/0252888 A1* | 10/2012 | Pantzaris ............ A61K 9/0095 514/458 |
| 2012/0258168 A1 | 10/2012 | Montesinos |
| 2013/0011469 A1 | 1/2013 | Minatelli et al. |
| 2013/0245119 A1 | 9/2013 | Harauma et al. |
| 2014/0024625 A1 | 1/2014 | Smith et al. |

OTHER PUBLICATIONS

J.P. Schuchardt et al., Moderate doses of EPA and DHA from re-esterified triacylglycerols but not from ethyl-esters lower fasting serum triaclyglycerols in statin-treated dyslipidemic subjects: Results from six month randomized controlled trial, plefa, vol. 85, Issue 6, pp. 381-386, Dec. 2011.

J. Neubronner et al., Enhanced increase of omega-3 index in response to long-term n-3 fatty acid supplementation from triacylglycerides verses ethyl esters, European Journal of Clinical Nutrition 65, pp. 247-254 (Feb. 2011), doi:10.1038/ejcn.2010.239.

Jadwiga C. Wojtowicz et al., Pilot, Prospective, Randomized, Double-masked, Placebo-controlled Clinical Trial of an Omega-3 Supplement for Dry Eye, Cornea, (2010).

J. Dyerbert et al, Bioavailability of marine n-3 fatty acid formulations, Prostaglandins Leukotrienes Essent. Fatty Acids (2010), doi:10.1016/j.plefa.2010.06.007.

Robert S. Chapkin et al., Dietary docosahexaenoic and eicosapentaenoic acid: Emerging mediators of Inflammation, Prostaglandins Leukotrienes Essent. Fatty Acids (2009), doi:10.1016/j.plefa.2009.05.010.

J. Thomas Brenna et al, α-Linolenic acid supplementation and conversion to n-3 long-chain polyunsaturated fatty acids in humans, Prostaglandins Leukotrienes Essent. Fatty Acids (2009), doi:10.1016/j.plefa.2009.01.004.

Charles N. Serhan et al., Maresins: novel macrophage mediators with potent antiinflammatory and proresolving actions, J. Exxp. Med., vol. 206, No. 1 (2008).

Marian S Macsai, The Role of Omega-3 Dietary Supplementation in Blepharitis and Meibomian Gland Dysfunction (An AOS Thesis), Trans Am Ophthalmol Soc, vol. 106 (2008).

Igor A. Butovich et al., Lipids of human meibum: mass-spectrometric analysis and structural elucidation, Journal of Lipid Research, vol. 48 (2007).

Sullivan et al., Third International Conference on the Lacrimal Gland, Tear Film and Dry Eye Syndrome: Basic Science and Clinical Relevance, Maui, Hi., Nov. 15-18, 2000.

http://seniorjournal.com/NEWS/Nutrition-Vitamins/2007/7-05-14-0mega3FattyAcids.htm (2013).

http://www.umm.edu/altmed/articles/macular-degeneration-000104.htm (2013).

http://www.aboutomega3.com/omega_3_and_macular_degeneration_-_what_you_need_to_know.html (2013).

http://www.medrounds.org/amd/2005/08/lutein-zeaxanthin-and-omega-3-poly.html (2013).

http://www.futurepundit.com/archives/006299.html (2013).

hittp://www.ncbi.nlm.nih.gov/pubmed/16815401 (2013).

http://ezinearticles.com/?Omega-3-Study-For-Macular-Degeneration&id=4312997 (2013).

http://www.emaxhealth.com/1275/96/34058/omega-3-helps-prevent-macular-degeneration.html (2013).

\* cited by examiner

METHODS FOR TREATING DRY EYE

RELATED APPLICATIONS

This continuation application claims the benefit of U.S. patent application Ser. No. 15/197,212, filed on Jun. 29, 2016 and entitled "COMPOSITIONS AND METHODS FOR USING SAME FOR REDUCING LEVELS OF ARACHIDONIC ACID IN TISSUE HAVING UNDERGONE AN INVASIVE PROCEDURE," which claims the benefit of U.S. patent application Ser. No. 13/815,599, filed on Mar. 12, 2013 and entitled "METHODS FOR IMPROVING THE QUALITY OF THE MEIBUM COMPOSITION OF MEIBOMIAN GLANDS" (now issued as U.S. Pat. No. 9,381,183), which claims the benefit of U.S. patent application Ser. No. 13/507,673, filed on Jul. 18, 2012 and entitled "COMPOSITIONS FOR IMPROVING THE QUALITY OF THE MEIBUM COMPOSITION OF INFLAMED OR DYSFUNCTIONAL MEIBOMIAN GLANDS" (now issued as U.S. Pat. No. 9,115,078), which claims the benefit of U.S. Provisional Patent Application Ser. No. 61/572,574, filed on Jul. 18, 2011 and entitled "COMPOSITIONS AND METHODS FOR USING SAME FOR TREATING POSTERIOR BLEPHARITIS."

BACKGROUND

The Field of the Invention

This invention relates to methods for improving and enhancing the lipid layer of the tear and increasing tear breakup time by way of elevating the omega-3 index in patients suffering from symptoms of dry eye, posterior blepharitis and/or meibomian gland dysfunction and, more specifically, to methods for administering a supplementation of omega-3 fatty acids to a patient having an inflamed meibomian gland so as to facilitate an increase in the amount of omega-3's acting as an anti-inflammatory and, respectively, decrease the amount of omega-6's acting as an inflammatory in the meibum composition, thereby normalizing the lipid layer of the tear and effectively reducing or eliminating the symptoms of dry eye, posterior blepharitis and/or meibomian gland dysfunction.

The Background Art

Dry eye is a condition in which there are insufficient tears to lubricate and nourish the eye. Tears are necessary for maintaining the health of the front surface of the eye and for providing clear vision. People with dry eyes either do not produce enough tears or have a poor quality of tears. With each blink of the eyelids, tears are spread across the cornea in order to provide lubrication, to wash away any foreign matter and to keep the surface of the eyes smooth and clear.

Tears are produced by several glands in and around the eyelids. When the normal amount of tear production decreases or tears evaporate too quickly from the corneal surface, symptoms of dry eye can develop.

As appreciated, tears are made up of oil, water and mucus. Each component serves a specified function in protecting and nourishing the front surface of the eye. A smooth oil layer helps to prevent evaporation of the water layer, while the mucin layer functions in spreading the tears evenly over the surface of the eye. If the tears evaporate too quickly or do not spread evenly over the cornea as a result of deficiencies with any of the three tear layers, symptoms of dry eye or posterior blepharitis may ensue.

Along the margin of the eyelids are a series of small sebaceous glands called meibomian glands. The meibomian glands create and distribute a supply of meibum, an oily substance, that makes up the lipid layer of the tear. The supply of meibum functions to help keep the eye moist and tends to protect the tear film from evaporation. There are approximately twenty-five meibomian glands on the upper eyelids and twenty-five meibomian glands on the lower eyelids. Upon blinking of the eye, the upper eyelid comes down, presses on the oily substance produced by the meibomian glands, and pulls a sheet of this oily substance upwards, thereby coating the tear layer beneath to keep it from evaporating. This oily substance or meibum (wherein lipids are a major component) which is created by the meibomian glands is therefore critical for healthy eyes and clear vision.

Meibomianitis refers to inflammation or dysfunction of the meibomian glands which is also referred to in the art as meibomian gland dysfunction. Inflammation of the meibomian glands may occur because of the production of meibum which is pro-inflammatory in nature as a result of an increased composition of omega-6 essential fatty acids. Secondarily, bacteria have been found to invade the meibomian glands and colonize there. Once inflamed, the meibomian glands generally will not function in a manner sufficient to adequately produce the quantity and quality of oils necessary to properly lubricate the eye.

The volume of oil produced from inflamed meibomian glands tends to decrease and the oils that are produced become thicker in composition, like toothpaste. These oils also become abnormal in their characteristics. Instead of spreading evenly across the aqueous layer, the oil coalesces leaving areas on the corneal surface in which the aqueous can evaporate and other areas in which the oil adheres to the cornea surface itself. This creates a dry spot on the cornea for which the aqueous cannot penetrate. Such condition generally produces a foreign body sensation and if it persists may result in injury to the epithelium which is seen as corneal staining on examination. A reduction in oil production therefore inherently results in a quantitative decrease in the quality and quantity of the oily layer, thus causing tears to evaporate more rapidly. Because the thickened oil does not coat the eye properly, a person with inflamed meibomian glands may experience discomfort or problems with their eyes that may include, for example, but not by way of limitation: (1) dryness; (2) burning; (3) itching; (4) irritation and redness; (5) blurred vision; and/or (6) foreign body sensations.

This inflammatory process can also spread throughout the lid margin and spill over to involve the ocular surface resulting in significant ocular discomfort Inflammation of the meibomian glands in the upper and lower lids can further lead to vascularization and fibrosis, causing stenosis and then closure of the meibomian gland orifices. Deprived of the meibum or lipids that inhibit evaporation, tear film evaporation will generally increase. Similarly, a deficiency in tear film generally results in irritation of the eye, but can also cause damage to the surface of the eye. As appreciated, an irregular oil pattern disrupts tears and allows for increased exposure of the aqueous layer to the atmosphere and the increased evaporation of the aqueous. Unfortunately, this inflamed condition of the meibomian glands has often been found to be chronic.

Some of the treatments for meibomianitis that have been contemplated by those skilled in the art include: (1) the application of artificial tears; (2) cleaning the affected eyelid margins with a gentle baby shampoo; and (3) applying warm and moist compresses 5-10 minutes two to three times per day in an effort to promote normal eyelid glandular function. A physician may also prescribe a topical and/or oral antibiotic such as, for example, tetracycline, erythromycin, or doxycycline, to help eradicate the bacteria found in the glands and to facilitate a breakdown in the thickened lipid secretions from the meibomian glands. These various treatments, however, can often take months before a treated patient notices any significant improvement.

Although the elimination of bacteria or anti-inflammatory effects of the antibiotics resulted in a temporary change, none of the known treatment methodologies have brought long-lasting relief to patients. Hoping to provide a form of sustainable relief to the ongoing symptoms associated with dry eye, with or without meibomian gland dysfunction, that are suffered by patients, a study was conducted by those skilled in the art to investigate the effects of dietary supplementation of a combination of flaxseed and fish oils on the tear film and the ocular surface. At the baseline, all patients in the study had a history of dry eye or one or more symptoms of posterior blepharitis. At the end of the study, the clinical results did not achieve any statistical significance, wherein the lipid composition of the samples collected from the omega-3 supplemented group was found to be very similar to that collected from the placebo group. Thus, the study concluded that dietary supplementation of flaxseed oil and omega-3 fatty acids for treating dry eye or meibomianitis showed no significant effect on meibum composition or aqueous tear evaporation rate.

Consistent with the foregoing, in order to control or resolve the long term effects of dry eye, posterior blepharitis, or meibomian gland dysfunction, the characteristics or nature of the oil (meibum) that is produced by the meibomian glands must be normalized. Thus, what is needed are nutritional or dietary supplement compositions and treatment methodologies using the same that effectively change the quality of the meibum composition, thereby resulting in a meibum composition having a direct correlation to enhancing and improving the function and/or composition of the lipid layer of the tear which reduces the symptoms associated with dry eye, posterior blepharitis and/or meibomian gland dysfunction.

SUMMARY AND OBJECTS OF THE INVENTION

In view of the foregoing, it is a primary object of the present invention to provide methods for administering a supplementation of omega-3 fatty acids to a patient suffering from symptoms of dry eye, wherein the supplementation of omega-3 fatty acids is provided in an effective amount sufficient to facilitate an increase in the resulting omega-3's content of the treated meibomian glands, acting as an anti-inflammatory, and, respectively, in a decrease in the amount of resulting omega-6's (arachidonic acid), acting as an inflammatory, thereby having an affect on the normalization of the lipid layer of the tear and a corresponding reduction in the associated dry eye symptoms.

It is a further object of the present invention to provide methods for administering a supplementation of omega-3 fatty acids to a patient suffering from symptoms of posterior blepharitis, wherein the supplementation of omega-3 fatty acids in the re-esterified triglyceride form is provided in an effective amount sufficient to effectively change the quality of the meibum composition resulting in a meibum composition that improves or increases tear breakup time, reduces tear osmolarity, and elevates the omega-3 index, while eliminating or reducing the related symptoms of posterior blepharitis.

It is a still further object of the present invention to provide methods for administering a supplementation of omega-3 fatty acids to a patient suffering from symptoms of meibomianitis, wherein the supplementation of omega-3 fatty acids in the re-esterified triglyceride form is provided in an effective amount sufficient to effectively change the quality of the meibum composition resulting in a meibum composition that improves or increases tear breakup time, reduces tear osmolarity, and elevates the omega-3 index, while eliminating or reducing the related symptoms of meibomianitis.

Additionally, it is an object of the present invention to provide a method for changing the composition of the oil produced by sebaceous glands found in the body from pro-inflammatory omega-6 to anti-inflammatory omega-3, whereby normalizing the oil production of the treated gland by way of administering a supplementation of omega-3 fatty acids as taught by the present invention.

It is a further object of the present invention to provide a method for changing the composition of the oil (meibum) produced by meibomian glands from pro-inflammatory omega-6 to anti-inflammatory omega-3, whereby normalizing the oil production of the meibomian gland by way of administering a supplementation of omega-3 fatty acids as taught by the present invention.

It is also an object of the present invention to provide a method for treating acne by way of changing the composition of the oil (sebum) produced by sebaceous glands found in the skin from pro-inflammatory omega-6 to anti-inflammatory omega-3, whereby normalizing the oil production of the gland by way of administering an embodiment of a nutritional or dietary supplement composition as taught by the present invention.

It is a still further object of the present invention to provide a method for treating post surgical inflammation by preoperatively administering an embodiment of a nutritional or dietary supplement composition as taught by the present invention, whereby increasing the omega-3 level and decreasing the omega-6 (arachidonic acid) level within the cell wall thereby reducing post surgical inflammation by reducing the prostaglandin precursors and increasing the anti-inflammatory and resolvins available at the surgical site.

Consistent with the foregoing objects, the present invention is directed to methods for administering a supplementation of omega-3 fatty acids to a patient suffering from symptoms of dry eye, posterior blepharitis and/or meibomianitis. The supplementation of omega-3 fatty acids is administered in an amount formulated to change the composition of the oil (meibum) produced by meibomian glands from pro-inflammatory omega-6 to anti-inflammatory omega-3, whereby normalizing the oil production of the meibomian gland so as to improve or increase tear break up time, reduce tear osmolarity, and elevate the omega-3 index, thereby, consequently, eliminating or reducing the related symptoms of dry eye, posterior blepharitis or meibomianitis (meibomian gland dysfunction).

In an embodiment of the present invention, the present invention provides for methods for treating and preventing dry eye associated with meibomian gland inflammation or dysfunction by way of administering a nutritional or dietary supplement composition comprising an effective amount of omega-3 fatty acids. The supplementation may include an effective amount of omega-3 fatty acids comprising a daily dosage that includes between about 600 mg and about 5,000 mg. The effective amount of omega-3's may comprise the re-esterified triglyceride form.

The effective amount of omega-3 fatty acids may comprise an effective amount of eicosapentaenoic acid (EPA). In one embodiment of the present invention, the daily dosage of an effective amount of EPA may include an amount greater than 600 mg.

In yet another embodiment of the present invention, the effective amount of omega-3 fatty acids may comprise an effective amount of docosahexaenoic acid (DHA). The daily dosage of an effective amount of DHA may include an amount greater than 500 mg.

In certain embodiments of the present invention, an effective amount of omega-3 fatty acids may be delivered in a daily dosage that includes between about 2,000 mg and about 3,000 mg. This effective amount of omega-3 fatty acids may comprise an effective amount of eicosapentaenoic acid (EPA) and an effective amount of docosahexaenoic acid (DHA). Similarly, in one embodiment of the present invention, the daily dosage of an effective amount of EPA may include an amount between about 1,600 mg and about 2,500 mg and the daily dosage of an effective amount of DHA may include an amount between about 500 mg and about 900 mg.

An additional amount of omega-3 fatty acids may also be included in the administered composition. These additional omega-3 fatty acids may include a daily dosage amount of between about 400 mg and about 700 mg. Furthermore, the nutritional or dietary supplement composition of the present invention may include an effective amount of Vitamin D (as D3). Such effective amount of Vitamin D may comprise a daily dosage amount between about 500 IU and about 2,000 IU.

As contemplated herein, the administration of the dietary or nutritional supplement composition of the present invention to effectively change the quality of the meibum composition of the meibomian glands may be delivered by means of softgel, tablet, liquids, granules, microgranules, powders, or any other delivery system deemed effective.

DETAILED DESCRIPTION OF THE PREFERRED EMBODIMENTS

It will be readily understood that the components of the present invention, as generally described herein, could be modified, arranged and designed in a wide variety of different formulas. Thus, the following more detailed description of the embodiments of the composition and systems and methods of the present invention is not intended to limit the scope of the invention. The scope of the invention is as broad as claimed herein.

As used herein, the term "omega-3's in the re-esterified triglyceride form" includes omega-3's derived from marine and other sources. As appreciated, omega-3's in fish are present in the triglyceride form. Marine source fatty acids may undergo purification by the use of absorbents and molecular distillation to remove mercury and other heavy metals and pollutants that are usually prevalent in these sources. This purification process generally results in the omega-3's being in the ethyl ester form, which is how the vast majority of OTC omega-3 products are sold. The omega-3's derived from marine sources, as used in the studies and as contemplated by the present invention, underwent a further re-esterification step to restore the triglyceride group to the omega-3's (rTG). Consequently, this further step of re-esterification of the omega-3's greatly increased the body's ability to absorb the omega-3's as illustrated in the studies.

As used herein, the term "effective amount" includes the amount of omega-3 fatty acids which is capable of effectively changing the quality of the meibum concentration which has a direct correlation to improving the lipid layer of the tear, while eliminating or reducing the related symptoms of dry eye, posterior blepharitis and/or meibomianitis.

As used herein, the terms "dry eye, meibomianitis, meibomian gland dysfunction, posterior blepharitis and blepharitis" are to be considered as synonyms.

The present invention provides for methods for treating and preventing dry eye associated with meibomian gland inflammation or dysfunction by way of administering a nutritional or dietary supplement composition comprising an effective amount of omega-3 fatty acids. The supplementation may include an effective amount of omega-3 fatty acids comprising a daily dosage that includes between about 600 mg and about 5,000 mg.

This effective amount of omega-3 fatty acids may comprise an effective amount of eicosapentaenoic acid (EPA). In one embodiment of the present invention, the daily dosage of an effective amount of EPA may include an amount greater than 600 mg.

In yet another embodiment of the present invention, the effective amount of omega-3 fatty acids may comprise an effective amount of docosahexaenoic acid (DHA). The daily dosage of an effective amount of DHA may include an amount greater than 500 mg.

In certain embodiments, the dietary or nutritional supplementation may include an effective amount of omega-3 fatty acids comprising a daily dosage including an effective amount between about 2,000 mg and about 3,000 mg. This effective amount of omega-3 fatty acids may be comprised of an effective amount of eicosapentaenoic acid (EPA) and an effective amount of docosahexaenoic acid (DHA). In an embodiment of the present invention, the daily dosage of an effective amount of EPA may include an amount between about 1,600 mg and about 2,500 mg and the daily dosage of an effective amount DHA may include an amount between about 500 mg and about 900 mg.

As appreciated by those skilled in the art, the dietary or nutritional supplement composition of the present invention includes omega-3 fatty acids that may comprise, for example, but not by way of limitation, the triglyceride form, re-esterified triglyceride concentrates, the ethyl ester form, the free fatty acid form, the phospholipids form, or any other suitable form sufficient to effectively change the quality of the meibum composition of the meibomian glands which has a direct correlation to improving the lipid layer of the tear, while eliminating or reducing the related symptoms of dry eye or meibomianitis. It is contemplated herein that the supplementation of the omega-3's can be in a concentrated form, whereas up to 100% of the unit volume can be omega-3. In certain embodiments of the present invention, the dietary or nutritional supplement omega-3 composition administered for treating dry eye, posterior blepharitis, meibomianitis for changing the quality of the meibum concentration of inflamed or dysfunctional meibomian glands in order to improve or increase tear break up time, reduce tear osmolarity, and elevate the omega-3 index may comprise omega-3 fatty acids in the re-esterified triglyceride form.

The effective amount of eicosapentaenoic acid (EPA) and/or an effective amount of docosahexaenoic acid (DHA) included in the dietary or nutritional supplement of the present invention may be obtained from known sources, such as for example, and not by way of limitation, fish, algae, squid, yeast, and vegetable sources. It is further recognized that stearidonic acid is a precursor to EPA and DHA and that consuming a product rich in stearidonic acid may be used to achieve the benefits as disclosed herein.

In selected embodiments of the nutritional or dietary supplement composition of the present invention, an effective amount of EPA/DHA may be administered in one or more softgel capsules containing an amount in the range of between about 800 mg and 1,250 mg and between about 250 mg and about 450 mg, respectively. For purposes of dosage, in certain embodiments of the present invention, the daily dosage amount may include an effective amount of EPA/DHA comprising the amounts of 840 mg and 280 mg, respectively.

In certain embodiments, this effective amount of EPA/DHA form may comprises a ratio of EPA/DHA of 3:1. Whereas, in selected embodiments, the ratio of EPA/DHA in each capsule may be in the range of between about 800 mg and 1,250 mg of EPA and between about 250 mg and 450 mg of DHA, whereby two capsules would comprise a daily effective dosage range.

An additional amount of omega-3 fatty acids may also be included in the administered composition. These additional omega-3 fatty acids may include a daily dosage amount of between about 400 mg and about 700 mg.

Furthermore, the nutritional or dietary supplement composition of the present invention may include an effective amount of Vitamin D (as D3). Such effective amount of Vitamin D may comprise a daily dosage amount of between about 500 IU and about 2,000 IU.

A clinical study was conducted based on the following parameters:

Objective:

To evaluate the clinical effect of the oral administration of a supplementation of omega-3 fatty acids in the re-esterified triglyceride form to a patient suffering from symptoms of dry eye and meibomian gland dysfunction.

Subjects:

A total of twenty-one (21) subjects or participants, between the ages of 18-60 years of age inclusive, who voluntarily provided written informed consent and who were capable of complying with the study visit schedule, were enrolled.

Visits:

There were three (3) scheduled visits with an attending physician. The first visit included an initial base line analysis for inclusion in the study. The second visit involved a 4-week follow-up and the third visit was an 8-week follow-up.

Study Population:

The parameters of the study protocol for the "inclusion" of participants included the following conditions: (1) the participant must be of the age of 18 to 60 at the time of signing the informed consent; (2) must understand, be willing and able, and likely to fully comply with study procedures, visit schedule, and restrictions; and (3) have symptoms of dry eye, posterior blepharitis, and/or meibomian gland dysfunction.

The parameters of the study protocol for the "exclusion" of participants included the following conditions: (1) clinically significant eyelid deformity or eyelid movement disorder that is caused by conditions such as notch deformity, incomplete lid closure, entropion, ectropion, hordeola, or chalazia; (2) previous ocular disease leaving sequelae or requiring current topical eye therapy other than for DED, including, but not limited to: active corneal or conjunctival infection of the eye and ocular surface scarring; (3) active ocular or nasal allergy; (4) LASIK or PRK surgery that was performed within one (1) year of Visit 1 or at any time during the study; (5) ophthalmologic drop use within 2 hours of Visits 1, 2, or 3; (6) pregnancy or lactation at any time during the study; (7) abnormality of nasolacrimal drainage (by history); (8) previous Punctal plugs placement or cauterization; or (9) started or changed the dose of chronic systemic medication known to affect tear production including, but not limited to antihistamines, antidepressants, diuretics, corticosteroids or immuno-modulators within 30 days of Visit 1, 2, or 3

Study Design:

This is a single-center study of participants with signs and symptoms of dry eye undergoing nutritional therapy treatment with an amount of omega-3 fatty acids delivered in re-esterified triglyceride form over the course of three (3) visits with approximately 4-week intervals between each visit.

The following clinical tests were performed on each participant at baseline: (1) Ocular Surface Disease Index (OSDI) which is a survey based on an array of questions that are asked having a gradation scale for answers to score subjective symptoms and to distinguish between normal subjects and patients with dry eye disease (normal, mild to moderate, and severe) and effect on vision-related function; (2) Slit Lamp Examination which involves the use of a low-power microscope combined with a high-intensity light source that can be focused to shine in a thin beam so that the physician can examine the patient's eyes, especially the eyelids, cornea, conjunctiva, sclera and iris; (3) Corneal Staining which is an evaluation of epithelial integrity; (4) Tear Break Up Time (TBUT) which involves a method of determining the stability of the tear film and checking for evaporative dry eye by way of determining the time required for dry spots to appear on the corneal surface after blinking; (5) Tear Osmolarity (TearLab®) that involves measuring the concentration of the osmotic solution of the tear; (6) EPA and DHA red blood cell saturation using the HS Omega-3 Index (OmegaQuant®) performed by probing the meibomian glands with a Maskin probe for a meibum sample; and (7) blood omega-3 levels were obtained to ensure patient compliance with supplementation given.

The participants were placed on a supplementation of omega-3 fatty acids comprising a daily dosage amount of 2,668 mg in a re-esterified triglyceride form (rTG) dispensed in four 667 mg capsules, each containing 420 mg of EPA, 140 mg of DHA, 107 mg of other omega-3's and 250 mg of Vitamin D(D3).

The participants were reevaluated at the 4-week visit with all the baseline testing except the (1) HS Omega-3 Index (OmegaQuant®) and meibum analysis. At 8-weeks, the participants were reevaluated with all the testing conducted at the baseline and, in addition, a the Mastroda paddle was used to collect meibomian gland secretions from each participant.

Outcome:

Based on OSDI which was taken at baseline, all twenty-one (21) participants reported a reduction of their primary complaint and fourteen (14) of the twenty-one (21) patients became completely asymptomatic.

As illustrated in Table 1, the participant levels of arachidonic acid, a direct precursor to pro-inflammatory eicosanoid derivatives, decreased significantly (p<0.00004) from 12.2% at baseline to 10.3% at 8 weeks, as measured in the blood.

TABLE 1

RBC Hemoglobin—Omega-6
(Arachidonic Acid/Docosapentaenoic Acid)

| Patient | ARA → | C20:4n6/ Visit 1 | C20:4n6/ Visit 2 | DPA → | C22:5n6/ Visit 1 | C22:5n6/ Visit 2 |
|---|---|---|---|---|---|---|
| 1 |  | 9.03% | 8.63% |  | 0.23% | 0.14% |
| 2 |  | 10.48% | 10.56% |  | 0.40% | 0.51% |
| 3 |  | 12.55% | 10.35% |  | 0.45% | 0.27% |
| 4 |  | 13.81% | 10.63% |  | 0.38% | 0.37% |
| 5 |  | 11.98% | 11.09% |  | 0.32% | 0.27% |
| 6 |  | 12.35% | 11.16% |  | 0.68% | 0.42% |
| 7 |  | 13.04% | 10.54% |  | 0.65% | 0.33% |
| 8 |  | 13.48% | 11.13% |  | 0.30% | 0.26% |
| 9 |  | 11.01% | 8.93% |  | 0.45% | 0.24% |
| 10 |  | 10.79% | 9.80% |  | 0.22% | 0.11% |
| 11 |  | 11.41% | 10.95% |  | 0.30% | 0.20% |
| 12 |  | 14.40% | 11.14% |  | 0.73% | 0.41% |
| 13 |  | 12.92% | 10.33% |  | 0.46% | 0.14% |
| 14 |  | 12.64% | 10.38% |  | 0.57% | 0.30% |
| 15 |  | 14.68% | 10.78% |  | 0.53% | 0.19% |
| 16 |  | 10.84% | 8.48% |  | 0.37% | 0.25% |
| 17 |  | 11.15% | 8.33% |  | 0.36% | 0.17% |
| 18 |  | 12.61% | 10.74% |  | 0.28% | 0.26% |
| 19 |  | 12.25% | 10.59% |  | 0.27% | 0.18% |
| 20 |  | 10.83% | 8.63% |  | 0.31% | 0.27% |
| 21 |  | 14.70% | 13.30% |  | 0.43% | 0.22% |

(ARA = Arachidonic Acid;
C20:4n6 = Arachidonic Acid;
DPA = Docosapentaenoic Acid;
C22:5n6 = Docosapentaenoic Acid)

The participant levels of EPA increased significantly ($p<0.00000$) in the RBCs from baseline and at 8 weeks (0.8% and 3.2%, respectfully) and levels of DHA increased ($p<0.00349$) in the RBCs from baseline and 8 weeks (3.3% and 4.1%, respectfully), as shown in Table 2.

TABLE 2

RBC Hemoglobin—Omega-3
(Docosahexaenoic Acid/Eicosapentaenoic Acid)

| Patient # | DHA → | C22:6n3/ Visit 1 | C22:6n3/ Visit 2 | EPA → | C20:5n3/ Visit 1 | C20:5n3/ Visit 2 |
|---|---|---|---|---|---|---|
| 1 |  | 3.39% | 5.23% |  | 0.49% | 3.76% |
| 2 |  | 2.92% | 3.53% |  | 0.23% | 1.04% |
| 3 |  | 2.65% | 3.67% |  | 0.30% | 3.56% |
| 4 |  | 3.06% | 4.32% |  | 0.75% | 2.63% |
| 5 |  | 3.04% | 3.80% |  | 1.13% | 2.49% |
| 6 |  | 2.69% | 3.97% |  | 0.43% | 3.22% |
| 7 |  | 4.08% | 5.80% |  | 0.51% | 3.46% |
| 8 |  | 5.52% | 5.31% |  | 1.68% | 3.78% |
| 9 |  | 2.03% | 3.17% |  | 0.70% | 2.49% |
| 10 |  | 2.35% | 3.46% |  | 0.55% | 3.27% |
| 11 |  | 3.87% | 4.35% |  | 1.64% | 3.22% |
| 12 |  | 2.48% | 4.19% |  | 0.31% | 3.41% |
| 13 |  | 2.01% | 3.11% |  | 0.44% | 3.15% |
| 14 |  | 2.59% | 3.36% |  | 0.49% | 2.95% |
| 15 |  | 3.05% | 4.43% |  | 1.78% | 4.69% |
| 16 |  | 3.24% | 3.70% |  | 0.45% | 2.55% |
| 17 |  | 4.03% | 3.70% |  | 0.46% | 4.97% |
| 18 |  | 2.88% | 4.20% |  | 0.62% | 3.92% |
| 19 |  | 5.27% | 5.13% |  | 1.77% | 3.78% |
| 20 |  | 4.45% | 3.67% |  | 1.16% | 1.91% |
| 21 |  | 3.41% | 4.08% |  | 1.52% | 2.51% |

(DHA = Docosahexaenoic Acid;
C22:6n3 = Docosahexaenoic Acid;
EPA = Eicosapentaenoic Acid;
C20:5n3 = Eicosapentaenoic Acid)

Referring now to Table 3, the HS Omega-3 Index Scores are provided for each of the twenty-one (21) participants.

TABLE 3

HS Omega-3 Index Scores

| Patient # | HS Omega 3/Visit 1 Index Percentage | HS Omega 3/Visit 2 Index Percentage |
|---|---|---|
| 1 | 4.34% | 9.52% |
| 2 | 3.60% | 5.05% |
| 3 | 3.42% | 7.74% |
| 4 | 4.28% | 7.46% |
| 5 | 4.65% | 6.78% |
| 6 | 3.58% | 7.70% |
| 7 | 5.07% | 9.79% |
| 8 | 7.71% | 9.63% |
| 9 | 3.19% | 6.15% |
| 10 | 3.36% | 7.24% |
| 11 | 6.00% | 8.08% |
| 12 | 3.26% | 8.11% |
| 13 | 2.91% | 6.76% |
| 14 | 3.54% | 6.81% |
| 15 | 5.32% | 9.65% |
| 16 | 4.16% | 6.76% |
| 17 | 4.97% | 9.20% |
| 18 | 3.97% | 8.64% |
| 19 | 7.55% | 9.44% |
| 20 | 6.10% | 6.08% |
| 21 | 5.41% | 7.09% |

(HS-Omega-3 Index percentage = Red Blood Cell Membrane Saturation of Omega-3s)

Tear osmolarity decreased on average seventeen percent (17%) at the eight week exam period, as illustrated in Table 4.

TABLE 4

Tear Osmolarity

| Patient # | Visit 1 | Visit 2 | Visit 3 |
|---|---|---|---|
| 1 | 300/300 | 325/303 | 300/289 |
| 2 | 284/298 | Px missed appt | 315, 299 OD, 298 OS |
| 3 | 290/307 | 305/293 | 286/300 |
| 4 | 307/303 | 309/288 | 303/309 |
| 5 | 345/318 | 302/292 | 292/308 |
| 6 | 349/305 | 301/306 | 310/317 |
| 7 | 305/301 | 330, 302/292 | 305/303 |
| 8 | 337, below range, 311 | 323/297 | 320/334 |
| 9 | 308/298 | 300/315, 285 | 308/303 |
| 10 | 298/292 | 289/288 | 275/296 |
| 11 | 279/280 | 276/below range x2 | 300/280 |
| 12 | 311/302 | 309/292 | 312/298 |
| 13 | 307/321 | 306/287 | 309/309 |
| 14 | 301/304 | 301/319 | 300/305 |
| 15 | 282/295 | Px missed appt | Unable gtts instilled |
| 16 | 325/301 | 304/303 | 312/291 |
| 17 | 327/296, 301 | 290/282 | 295/299 |
| 18 | 280/295 | 294/299 | 303/302 |
| 19 | 305/303 | 309/300 | 314/306 |
| 20 | 282/285 | 285/276 | 280/286 |
| 21 | 297/291 | 294/294 | 281/292 |

(The osmolarity of the right eye/left eye in milliosmols)

As shown, there were variations in starting osmolarities among patients. The use of topical drops within two (2) hours of checking osmolarity disqualified participant 15's test as it may have had a dilution effect on the tears.

The lid margins were graded on a scale of trace—4 for meibomian gland insipisation. The results of the participants of the clinical study are illustrated in Table 5.

TABLE 5

| | Lid Margins | | |
|---|---|---|---|
| Patient # | Visit 1 | Visit 2 | Visit 3 |
| 1 | irregular | irreg | slight irreg |
| 2 | 1+ | missed appt | trace |
| 3 | tr-1 | trace | cl-tr |
| 4 | trace+ | clear-trace | clear |
| 5 | irreg | less irreg | tr irreg |
| 6 | trace | trace | cl-tr |
| 7 | tr+ | trace | tr |
| 8 | tr-1 | tr OD, tr-1 OS | tr OU |
| 9 | tr + w/foam | tr + w/foam | tr no foam |
| 10 | irreg | irreg | mild irreg |
| 11 | 1+ | tr+ | tr |
| 12 | tr-1 | tr-1 | tr-1 w/foam |
| 13 | tr | cl-tr | cl OD, tr OS |
| 14 | irreg | irreg | slight irreg |
| 15 | 3 + OD, 4 + OS | missed appt | 1 + OU |
| 16 | tr | Tr | cl-tr |
| 17 | tr OD, cl-tr OS | cl-tr/irreg | tr irreg |
| 18 | Tr/irreg | tr/irreg | mild irreg |
| 19 | tr-1 | tr OD, cl-tr OS | irreg |
| 20 | 1+ | tr-1 | tr+ |
| 21 | tr OD, tr-1 OS | tr OD, tr-1 OS | cl-tr OD, tr OS |

(Grading of meibomian gland appearance with reference to inspissation)

As shown, some patients did not have insipisation, but their lid margins were irregular versus smooth due to previous inflammation.

Referring now to Table 6, the improvement of Tear Break Up Time (TBUT) at eight weeks was statistically significant ($p<0.00027$).

TABLE 6

| | Tear Breakup Time | | | |
|---|---|---|---|---|
| Patient # | Visit 1 | Visit 2 | Visit 3 | |
| 1 | 2-3 sec OD, OS | 3-4 sec OD, OS | 4-5 OD, 3-4 OS | |
| 2 | 3 OD, OS, SPK OS > OD | missed appt | 4 OD, OS no SPK OD, tr OS | |
| 3 | 3 sec OD, OS | 3-4 OD, 2-3 OS | 3 sec OU | no SPK on any visit |
| 4 | 3 sec OU, SPK OD | 3 OD, 4 OS, tr SPK OD | 4-5 OU, no SPK | |
| 5 | not noted, SPK OS > OD | 4 OD, 5 OS tr SPK OU | 4-5sec OU no SPK | |
| 6 | 3 sec OU | 3 sec OU | 4-5 OD, 4 OS | no SPK on any visit |
| 7 | 3 OU, tr SPK OU | 3 OD, 4 OS, tr SPK OU | 3 OU, minimal SPK OU | |
| 8 | 3 OU, SPK OD/denseOS | 2-3 OU, Inf SPK OU | 3-4 OD, 3 OS, minimal SPK inf OU | |
| 9 | not noted, SPK OU | sec ou, no SPK | 4 sec OD, OS, no SPK | |
| 10 | 3-4 OD, 2 OS, SPKOD > OD | 4 OD, 2-3 OS, tr SPK OS | 4 OD, 3 OS, tr SPK OS | |
| 11 | 2-3 OD, 3 OS, no SPK | not noted, no SPK | 3 OU, minimal SPK OU | |
| 12 | not noted | 3 sec OU | 4-5 sec OU | |
| 13 | 3-4 OD, 2-3 OS, SPK OS | 4 OD, 3 OS, no SPK | 4 OU, no SPK | |
| 14 | 1-2 OU, inf SPK OU | 4 OD, 3 OS, Inf SPK OU | 2-3 OD, 3 OS, tr SPK OU | |
| 15 | Corneal Abrasions OU | missed appt | OD clear, Lt irreg | |
| 16 | 3 OU, tr SPK OU | 4 OU, tr SPK OU | 4 sec OU, no SPK OD, tr OS | |
| 17 | 3 OU, Inf SPK OU | 3 OU, tr SPK OU | 4 OD, 3-4 OS, sm tr SPK OU | |
| 18 | 3 OU, dense SPK OU | 4 OU, no SPK OU | 3 OU, tr inf SPK OU | |
| 19 | 3-4 OD, 3 OS no SPK OU | 3 OD, 4-5 OS, tr SPK OD | 3-4 OU, tr inf SPK OU | |
| 20 | 3 OU, no SPK | 4-5 OU, mild SPK OU | 4 OU, no SPK | |
| 21 | 2 OU, no SPK | 2-3 OU, no SPK OU | 3-4 OU, tr inf SPK OU | |

(Tear breakup time in seconds)

As shown, fifteen (15) of nineteen (19) participants demonstrated a lengthening of their TBUT from baseline.

As illustrated in Tables 7 and 8, meibum analysis from the initial samples from the study participants revealed that thirteen (13) participants had insufficient quantity of oil to analyze. Of the seven (7) that were readable, none of the participants exhibited omega-3 fatty acids in the meibum. Bacterial components comprised 10 to 15% of the oils present. Oleic acid (18:1 w9c) comprised between 34% and 60%.

TABLE 7

| Meibum Analysis (BEFORE) | | | |
|---|---|---|---|
| Volume | DATASM | Method | PLFA2 |
| SeqName | E11413599T | Start Time | Apr. 13, 2011 15:12 |
| Samp# | 4 | Prof Method | PLFA2 |
| Samp ID | UN-SMITH11-04 | Total Response | 49827.85137 |

TABLE 7-continued

Meibum Analysis (BEFORE)

| | | | | | |
|---|---|---|---|---|---|
| ID# | (02-slide# 2 17-PCN) | | Total Named | | 36290.30992 |
| Bottle: | 4184 | | Percent Named | | 72.83137627 |
| Seq# | 5 | | Total Amount | | 36377.84812 |
| SampType | 4184 | | Comment | | Total response less than |
| | sample | | | | 50000.0. C |

Total response less than 50000.0. Concentrate and re-run.

| RT | Response | Ar/Ht | RFact | ECL | Peak Name | Percent | Comment1 | Comment2 |
|---|---|---|---|---|---|---|---|---|
| 0.787 | ######## | 0.015 | 0.000 | 7.688 | SOLVENT PEAK | 0.00 | <min rt | |
| 0.975 | 13072 | 0.014 | 0.000 | 8.663 | | 0.00 | <min rt | |
| 2.454 | 959 | 0.014 | 1.070 | 13.999 | 14:0 | 2.82 | ECL deviates −0.001 | Reference −0.003 |
| 2.969 | 583 | 0.013 | 1.040 | 15.002 | 15:0 | 1.67 | ECL deviates 0.002 | Reference −0.003 |
| 3.300 | 942 | 0.017 | 0.000 | 15.560 | | 0.00 | | |
| 3.338 | 942 | 0.013 | 1.025 | 15.624 | 16:0 iso | 2.65 | ECL deviates −0.010 | |
| 3.443 | 3745 | 0.023 | 1.022 | 15.800 | 16:1 w9c | 10.52 | ECL deviates 0.004 | |
| 3.564 | 4592 | 0.015 | 1.017 | 16.003 | 16:0 | 12.84 | ECL deviates 0.003 | Reference −0.003 |
| 4.037 | 1582 | 0.014 | 1.005 | 16.725 | 17:0 anteiso | 4.37 | ECL deviates −0.008 | Reference −0.016 |
| 4.087 | 825 | 0.015 | 0.000 | 16.801 | | 0.00 | | |
| 4.627 | 1432 | 0.015 | 0.994 | 17.584 | 18:3 w6c (6, 9, 12) | 3.91 | ECL deviates −0.004 | |
| 4.732 | 3727 | 0.017 | 0.993 | 17.734 | 18:2 w6, 9c | 10.17 | ECL deviates 0.007 | |
| 4.765 | 13444 | 0.018 | 0.992 | 17.780 | 18:1 w9c | 36.67 | ECL deviates 0.000 | |
| 4.802 | 2671 | 0.017 | 0.992 | 17.833 | 18:1 w9t. | 7.28 | ECL deviates 0.008 | |
| 4.923 | 1777 | 0.015 | 0.990 | 18.005 | 18:0 | 4.84 | ECL deviates 0.005 | Reference −0.004 |
| 6.121 | 836 | 0.019 | 0.981 | 19.637 | 20:0 iso | 2.25 | ECL deviates −0.001 | Reference −0.012 |
| 6.694 | 4042 | 0.020 | 0.000 | 20.409 | | 0.00 | | |
| 6.940 | 683 | 0.017 | 0.000 | 20.741 | | 0.00 | | |
| 8.072 | 4044 | 0.017 | 0.000 | 22.283 | Phthalate | 0.00 | ECL deviates 0.000 | |
| 8.793 | 2920 | 0.017 | 0.000 | 23.288 | | 0.00 | | |
| 9.053 | 1571 | 0.026 | 0.000 | 23.655 | | 0.00 | | |
| 9.507 | 774 | 0.018 | 0.000 | 24.297 | | 0.00 | | |
| 9.582 | 1780 | 0.014 | 0.000 | 24.403 | | 0.00 | | |

(Iso and anti-iso represent bacterial components)

TABLE 8

Meibum Analysis (AFTER)
(DHA 22:6w3, 9, 6, 12, 15 present at 3% post treatment)
On page 25, please replace Table 8 with the following:

| | | | | | |
|---|---|---|---|---|---|
| Volume | DATASM | | Method | | PLFA2 |
| SeqName | E11 412 592T | | Start Time | | Apr. 12, 2011 15:18 |
| Samp# | 5 | | Prof Method | | PLFA2 |
| Samp ID | UN-SMITH-04 (108-CN) | | Total Response | | 111929.9264 |
| ID# | 4177 | | Total Named | | 71882.51325 |
| Bottle: | 6 | | Percent Named | | 64.22099569 |
| Seq# | 4177 | | Total Amount | | 71928.91226 |
| SampType | sample | | Comment | | |

| RT | Response | Ar/Ht | RFact | ECL | Peak Name | Percent | Comment1 | Comment2 |
|---|---|---|---|---|---|---|---|---|
| 0.781 | 56879 | 0.006 | 0.000 | 7.646 | | 0.00 | <min rt | |
| 0.789 | ######## | 0.021 | 0.000 | 7.685 | SOLVENT PEAK | 0.00 | <min rt | |
| 0.979 | 10310 | 0.017 | 0.000 | 8.670 | | 0.00 | <min rt | |
| 3.223 | 1064 | 0.013 | 0.000 | 15.436 | | 0.00 | | |
| 3.340 | 2113 | 0.013 | 1.031 | 15.632 | 16:0 iso | 3.03 | ECL deviates −0.002 | |
| 3.437 | 1521 | 0.013 | 1.027 | 15.793 | 16:1 w9c | 2.17 | ECL deviates −0.003 | |
| 3.460 | 4711 | 0.016 | 1.027 | 15.832 | 16:1 w7c | 6.72 | ECL deviates 0.008 | |
| 3.565 | 1796 | 0.014 | 1.023 | 16.007 | 16:0 | 2.55 | ECL deviates 0.007 | Reference −0.004 |
| 3.900 | 1163 | 0.015 | 1.014 | 16.515 | Sum in Feature 1 | 1.64 | ECL deviates 0.003 | 17:1 anteiso B/iso |
| 3.976 | 801 | 0.017 | 1.012 | 16.630 | 17:0 iso | 1.13 | ECL deviates −0.006 | Reference −0.013 |
| 4.038 | 4088 | 0.016 | 1.010 | 16.724 | 17:0 anteiso | 5.74 | ECL deviates −0.009 | Reference −0.016 |
| 4.089 | 682 | 0.016 | 0.000 | 16.802 | | 0.00 | | |
| 4.511 | 1003 | 0.017 | 1.000 | 17.415 | 17:0 10-methyl | 1.39 | ECL deviates 0.002 | |
| 4.630 | 1125 | 0.017 | 0.998 | 17.584 | 18:3 w6c (6, 9, 12) | 1.56 | ECL deviates −0.004 | |
| 4.672 | 2782 | 0.020 | 0.998 | 17.644 | 18:0 iso | 3.86 | ECL deviates 0.008 | Reference 0.003 |
| 4.701 | 712 | 0.013 | 0.000 | 17.685 | | 3.00 | | |
| 4.733 | 1259 | 0.013 | 0.997 | 17.730 | 18:2 w6 9c | 1.74 | ECL deviates 0.003 | |
| 4.766 | 36466 | 0.017 | 0.996 | 17.777 | 18:1 w9c | 50.50 | ECL deviates −0.004 | |
| 4.803 | 7466 | 0.018 | 0.996 | 17.830 | 18:1 w9t | 10.33 | ECL deviates 0.005 | |
| 4.924 | 1026 | 0.015 | 0.994 | 18.001 | 18:0 | 1.42 | ECL deviates 0.001 | Reference −0.004 |
| 5.271 | 760 | 0.015 | 0.000 | 18.479 | | 3.00 | | |
| 5.827 | 2480 | 0.017 | 0.000 | 19.241 | | 3.00 | | |
| 6.120 | 1703 | 0.020 | 0.982 | 19.637 | 20:0 iso | 2.32 | ECL deviates −0.001 | Reference −0.014 |
| 6.274 | 670 | 0.014 | 0.981 | 19.845 | 20:1 w7c | 3.91 | ECL deviates −0.005 | |

TABLE 8-continued

Meibum Analysis (AFTER)
(DHA 22:6w3, 9, 6, 12, 15 present at 3% post treatment)
On page 25, please replace Table 8 with the following:

| | | | | | | | |
|---|---|---|---|---|---|---|---|
| 6.655 | 1360 | 0.017 | 0.000 | 20.365 | | 3.00 | |
| 6.693 | 2697 | 0.018 | 0.000 | 20.417 | | 3.00 | |
| 6.732 | 804 | 0.019 | 0.000 | 20.470 | | 3.00 | |
| 6.942 | 826 | 0.015 | 0.000 | 20.743 | | 3.00 | |
| 7.327 | 2191 | 0.017 | 0.976 | 21.264 | 22:6 w3, 9, 6, 12, 15 | 2.97 | ECL deviates 0.003 |
| 7.603 | 893 | 0.016 | 0.000 | 21.638 | | 3.00 | |
| 8.073 | 2745 | 0.018 | 0.000 | 22.281 | Phthalate | 3.00 | ECL deviates −0.002 |
| 8.149 | 1680 | 0.018 | 0.000 | 22.386 | | 3.00 | |
| 8.795 | 10815 | 0.020 | 0.000 | 23.286 | | 3.00 | |
| 8.908 | 2329 | 0.018 | 0.000 | 23.446 | | 3.00 | |
| 8.958 | 3193 | 0.018 | 0.000 | 23.517 | | 3.00 | |
| 9.055 | 3361 | 0.027 | 0.000 | 23.652 | | 3.00 | |
| 9.511 | 2058 | 0.018 | 0.000 | 24.295 | | 3.00 | |
| 9.584 | 4335 | 0.015 | 0.000 | 24.397 | | 3.00 | |
| 1.000 | 1163 | 0.000 | 0.000 | 0.000 | Summed Feature | 1.64 | 17:1 Iso/anteiso B  17:1 anteiso B/Iso |

At the eight weeks exam period, fourteen (14) of the twenty-one (21) meibum samples had sufficient quantity to analyze. All fourteen (14) meibum samples had DHA (22:6n-3) present. The DHA was present as approximately 2% to 3% of the meibum composition.

Corneal staining was graded on a scale of trace, 1+, 2+, 3+, and 4+. Improving one grade was considered clinically significant. Nine (9) of twenty-one (21) patients did not present with corneal staining at baseline, but the eleven (11) patients that did all had significant improvement by way of slit lamp examination at the four week exam.

By end of the study, all participants showed improvement. Consequently, an increase in omega-3 RBC and meibum composition had a direct correlation to the improvement of tear break up time, reduction in tear osmolarity, and elevation of omega-3 index from the baseline. The study also demonstrated the new presence of omega-3 fatty acids within the meibum itself.

An additional clinical study was conducted based on the following parameters:

Objective:

To evaluate the clinical effect of the oral administration of a supplementation of omega-3 fatty acids in re-esterified triglyceride form on the meibum in patients suffering from symptoms of dry eye and meibomian gland dysfunction.

Subjects/Visits/Study Design:

Patients with meibomian gland dysfunction were selected from the clinic and a meibum sample was obtained from each of the participants using a Mastroda paddle at baseline and at 8-weeks. The samples were immediately frozen and shipped at a later date on dry ice to be analyzed by the OmegaQuant® system. The participants were placed on a supplementation of omega-3 fatty acids comprising a daily dosage amount of 2,668 mg in a re-esterified triglyceride form (rTG) dispensed in four 667 mg capsules, each containing 420 mg of EPA, 140 mg of DHA, 107 mg of other omega-3's and 250 mg of Vitamin D(D3).

Outcome:

Of the eighteen (18) available participant samples (three (3) samples appeared to be contaminated), twelve (12) showed an increase in the level of anti-inflammatory fatty acids (omega-3's) of almost five (5) fold and, more specifically, 4.85. The level of inflammatory fatty acids (omega-6's) decreased about two (2) fold. The results of the second study confirm the findings of the first study showing an increase in omega-3 in the meibum with the more accurate analytic system facilitated with by use of the OmegaQuant® system.

Furthermore, the findings of these studies indicate that on each blink a bath of inflammatory material, namely arachidonic acid (an omega-6) flows over the entire ocular surface. Here, lipases and other enzymes such as cyclooxygenase have the opportunity to break this chemical down into its prostaglandin derivatives, which are very potent inflammatory agents. When treated with oral supplementation of omega-3 in the re-esterified triglyceride form, the meibum is changed from an inflammatory bath with each blink to an anti-inflammatory bath. Reducing the inflammatory components about 2.5 fold would have a profound effect on the tissues continually bathed by the meibum, changing to an almost five (5) fold increase in anti-inflammatory would further stabilize the ocular surface. As taught by the present invention, bathing the ocular surface in an anti-inflammatory meibum instead of an inflammatory meibum is the mechanism of action of the supplementation of the omega-3 in re-esterified triglyceride form, delivered in the dosage amounts disclosed herein, such that said supplementation improved the resolution of dry eye symptoms, tear osmolarity, tear break up time, and blood saturation of omega.

The following examples will illustrate several embodiments of the present invention in further detail. It will be readily understood that the nutritional or dietary supplement composition of the present invention, as generally described and illustrated in the Examples herein, could be synthesized in a variety of formulations and dosage forms. Thus, the following more detailed description of the embodiments of the methods, formulations and compositions of the present invention, as represented in the Examples are not intended to limit the scope of the invention, as claimed, but it is merely representative of various contemplated embodiments of the present invention.

EXAMPLE I

A daily dosage formulation of an embodiment of the nutritional or dietary supplement composition of the present invention administered for an increase in the omega-3 level and a decrease in the omega-6 in the meibum composition of the meibomian glands is set forth as comprising:

Omega-3 fatty acids 600 mg-5,000 mg

In certain embodiments of the present invention, a method for changing the quality of a meibum concentration of inflamed or dysfunctional meibomian glands comprises administering a supplementation comprising an effective amount of omega-3 fatty acids as disclosed in Example I, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE II

A daily dosage formulation of an embodiment of the nutritional or dietary supplement composition of the present invention administered for an increase in the omega-3 level and a decrease in the omega-6 in the meibum composition of the meibomian glands is set forth as comprising:
Omega-3 fatty acids 1,000 mg-3,000 mg
In certain embodiments of the present invention, a method for changing the quality of a meibum concentration of inflamed or dysfunctional meibomian glands comprises administering a supplementation comprising an effective amount of omega-3 fatty acids as disclosed in Example II, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE III

A daily dosage formulation of an embodiment of the nutritional or dietary supplement composition of the present invention administered for an increase in the omega-3 level and a decrease in the omega-6 in the meibum composition of the meibomian glands is set forth as comprising:
omega-3 fatty acids 2,000 mg-3,000 mg
In certain embodiments of the present invention, a method for changing the quality of a meibum concentration of inflamed or dysfunctional meibomian glands comprises administering a supplementation comprising an effective amount of omega-3 fatty acids as disclosed in Example III, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE IV

A daily dosage formulation of an embodiment of the nutritional or dietary supplement composition of the present invention administered for an increase in the omega-3 level and a decrease in the omega-6 in the meibum composition of the meibomian glands is set forth as comprising:
eicosapentaenoic acid (EPA)≥600 mg
docosahexaenoic acid (DHA)≥500 mg
In certain embodiments of the present invention, a method for changing the quality of a meibum concentration of inflamed or dysfunctional meibomian glands comprises administering a supplementation comprising an effective amount of omega-3 fatty acids as disclosed in Example IV, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE V

A daily dosage formulation of an embodiment of the nutritional or dietary supplement composition of the present invention administered for an increase in the omega-3 level and a decrease in the omega-6 in the meibum composition of the meibomian glands is set forth as comprising:
docosahexaenoic acid (DHA)≥500 mg
In certain embodiments of the present invention, a method for changing the quality of a meibum concentration of inflamed or dysfunctional meibomian glands comprises administering a supplementation comprising an effective amount of omega-3 fatty acids as disclosed in Example V, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE VI

A daily dosage formulation of an embodiment of the nutritional or dietary supplement composition of the present invention administered for an increase in the omega-3 level and a decrease in the omega-6 in the meibum composition of the meibomian glands is set forth as comprising:
eicosapentaenoic acid (EPA)≥600 mg
docosahexaenoic acid (DHA)≥500 mg
other omega-3 fatty acids 400 mg-700 mg
In certain embodiments of the present invention, a method for changing the quality of a meibum concentration of inflamed or dysfunctional meibomian glands comprises administering a supplementation comprising an effective amount of omega-3 fatty acids as disclosed in Example VI, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3.

In certain embodiments, the omega-3 fatty acids comprise the esterified or re-esterified triglyceride form.

EXAMPLE VII

A daily dosage formulation of an embodiment of the nutritional or dietary supplement composition of the present invention administered for an increase in the omega-3 level and a decrease in the omega-6 in the meibum composition of the meibomian glands is set forth as comprising:
  eicosapentaenoic acid (EPA) 1,600 mg-2,500 mg
  docosahexaenoic acid (DHA) 500 mg-900 mg
  other omega-3 fatty acids 400 mg-700 mg
In certain embodiments of the present invention, a method for changing the quality of a meibum concentration of inflamed or dysfunctional meibomian glands comprises administering a supplementation comprising an effective amount of omega-3 fatty acids as disclosed in Example VII, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE VIII

A daily dosage formulation of an embodiment of the nutritional or dietary supplement composition of the present invention administered for an increase in the omega-3 level and a decrease in the omega-6 in the meibum composition of the meibomian glands is set forth as comprising:
  eicosapentaenoic acid (EPA)≥600 mg
  docosahexaenoic acid (DHA)≥500 mg
  Vitamin D (as D3) 500 IU-2,000 IU
In certain embodiments of the present invention, a method for changing the quality of a meibum concentration of inflamed or dysfunctional meibomian glands comprises administering a supplementation comprising an effective amount of omega-3 fatty acids as disclosed in Example VIII, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE IX

A daily dosage formulation of an embodiment of the nutritional or dietary supplement composition of the present invention administered for an increase in the omega-3 level and a decrease in the omega-6 in the meibum composition of the meibomian glands is set forth as comprising:
  eicosapentaenoic acid (EPA) 1,600 mg-2,500 mg
  docosahexaenoic acid (DHA) 500 mg-900 mg
  Vitamin D (as D3) 500 IU-2,000 IU
In certain embodiments of the present invention, a method for changing the quality of a meibum concentration of inflamed or dysfunctional meibomian glands comprises administering a supplementation comprising an effective amount of omega-3 fatty acids as disclosed in Example IX, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE X

A daily dosage formulation of an embodiment of the nutritional or dietary supplement composition of the present invention administered for an increase in the omega-3 level and a decrease in the omega-6 in the meibum composition of the meibomian glands is set forth as comprising:
  eicosapentaenoic acid (EPA)≥600 mg
  docosahexaenoic acid (DHA)≥500 mg
  other omega-3 fatty acids 400 mg-700 mg
  Vitamin D (as D3) 500 IU-2,000 IU
In certain embodiments of the present invention, a method for changing the quality of a meibum concentration of inflamed or dysfunctional meibomian glands comprises administering a supplementation comprising an effective amount of omega-3 fatty acids as disclosed in Example X, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE XI

A daily dosage formulation of an embodiment of the nutritional or dietary supplement composition of the present invention administered for an increase in the omega-3 level and a decrease in the omega-6 in the meibum composition of the meibomian glands is set forth as comprising:
  eicosapentaenoic acid (EPA) 1,600 mg-2,500 mg
  docosahexaenoic acid (DHA) 500 mg-900 mg
  other omega-3 fatty acids 400 mg-700 mg
  Vitamin D (as D3) 500 IU-2,000 IU
In certain embodiments of the present invention, a method for changing the quality of a meibum concentration of inflamed or dysfunctional meibomian glands comprises administering a supplementation comprising an effective amount of omega-3 fatty acids as disclosed in Example XI, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3.

In certain embodiments, the omega-3 fatty acids comprise the esterified or re-esterified triglyceride form.

EXAMPLE XII

A daily dosage formulation of an embodiment of the nutritional or dietary supplement composition of the present invention administered for an increase in the omega-3 level and a decrease in the omega-6 in the meibum composition of the meibomian glands is set forth as comprising:
eicosapentaenoic acid (EPA) 1,650 mg-1,750 mg
docosahexaenoic acid (DHA) 500 mg-600 mg
other omega-3 fatty acids 400 mg-500 mg
Vitamin D (as D3) 600 IU-800 IU In certain embodiments of the present invention, a method for changing the quality of a meibum concentration of inflamed or dysfunctional meibomian glands comprises administering a supplementation comprising an effective amount of omega-3 fatty acids as disclosed in Example XII, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

EXAMPLE XIII

A daily dosage formulation of an embodiment of the nutritional or dietary supplement composition of the present invention administered for an increase in the omega-3 level and a decrease in the omega-6 in the meibum composition of the meibomian glands is set forth as comprising:
eicosapentaenoic acid (EPA) 1,680 mg
docosahexaenoic acid (DHA) 560 mg
other omega-3 fatty acids 428 mg
Vitamin D (as D3) 334 IU In certain embodiments of the present invention, a method for changing the quality of a meibum concentration of inflamed or dysfunctional meibomian glands comprises administering a supplementation comprising an effective amount of omega-3 fatty acids as disclosed in Example XIII, wherein increasing levels of omega-3's and, respectively, decreasing levels of omega-6's in the meibum composition. Consequently, bathing the ocular surface in an anti-inflammatory meibum instead of an inflammatory meibum is the mechanism of action of the supplementation of the omega-3's delivered in the dosage amounts disclosed herein so as to improve the resolution of dry eye symptoms, tear osmolarity, tear break up time, and blood saturation of omega-3. In certain embodiments, the omega-3 fatty acids comprise the esterified or re-esterified triglyceride form.

As concluded from the studies conducted, the supplementation of omega-3's in the re-esterified triglyceride form has a three (3) phase affect in the inflamed meibomian gland. First, the level of omega-3 is increased which, respectively, competes with arachidonic acid (omega-6) for binding sites on cyclooxygenase. Secondly, the amount of arachidonic acid which leads to prostaglandin synthesis is reduced. The products of COX 1 & 2 enzymes working on omega-3 creates eicosanoids that compete with those in the prostaglandin pathway from the omega-6. Thirdly, the production of resolvin from the omega-3 may provide an even greater factor in the anti-inflammatory action within the meibomian glands. Consequently, the level of inflammatory fatty acids (omega-6's) decreased about two (2) fold and the level of anti-inflammatory fatty acids (omega-3's) increased nearly five (5) fold.

Consistent with the foregoing, certain embodiments of the present invention provide methods for changing the quality of the meibum concentration of inflamed or dysfunctional meibomian glands, comprising the steps of: (1) administering a supplementation comprising an effective amount of omega-3 fatty acids; (2) increasing levels of omega-3's in a composition of meibum of the treated meibomian glands; and (3) decreasing levels of omega-6's in said composition of meibum. Bathing the ocular surface in an anti-inflammatory meibum instead of an inflammatory meibum facilitates the mechanism of action of the supplementation of the omega-3's delivered in the dosage amounts disclosed herein so as to eliminate or reduce the related symptoms of dry eye, posterior blepharitis, and/or meibomianitis, reduce tear osmolarity, improve or increase tear break up time, and/or elevate the omega-3 index.

The present invention may be embodied in other specific forms without departing from its fundamental functions or essential characteristics. The described embodiments are to be considered in all respects only as illustrative, and not restrictive. All changes which come within the meaning and range of equivalency of the illustrative embodiments are to be embraced within their scope.

What is claimed and desired to be secured by the United States Letters Patent is:

1. A method for treating dry eye and improving the quality of the meibum composition of inflamed or dysfunctional meibomian glands of a mammal, comprising the steps of:
administering a composition consisting essentially of an effective amount of omega-3 fatty acids on a daily dosage basis to said mammal having inflamed or dysfunctional meibomian glands, wherein said amount of omega-3 fatty acids comprises eicosapentaenoic acid (EPA) in an amount greater than 600 mg and in the re-esterified triglyceride form; and wherein said composition is devoid of omega-6 fatty acids;
increasing levels of anti-inflammatory omega-3's in the meibum composition of said treated meibomian glands of said mammal; and
decreasing levels of inflammatory omega-6's in the meibum composition of said treated meibomian glands.

2. The method as defined in claim 1, further comprising the steps of taking a baseline measurement of tear break up time of said mammal prior to administering said composition and taking a second measurement of tear break up time of said mammal after administration of said composition to evaluate an improvement of tear break up time of said mammal as compared to said corresponding baseline measurement.

3. The method as defined in claim 1, further comprising the steps of taking a baseline measurement of tear osmolarity of said mammal prior to administering said composition and taking a second measurement of tear osmolarity of said mammal after administration of said composition to evaluate a reduction of tear osmolarity of said mammal as compared to said corresponding baseline measurement.

4. The method as defined in claim 1, further comprising the steps of taking a baseline measurement of the quality of tears of said mammal prior to administering said composition and taking a second measurement of the quality of tears of said mammal after administration of said composition to evaluate an improvement in the quality of tears of said mammal as compared to said corresponding baseline measurement.

5. The method as defined in claim 1, wherein said amount of EPA comprises between 600 mg and 2,500 mg.

6. The method as defined in claim 1, wherein said amount of omega-3 fatty acids comprises an effective amount of docosahexaenoic acid (DHA).

7. The method as defined in claim 6, wherein said effective amount of DHA comprises an amount greater than 500 mg.

8. The method as defined in claim 6, wherein said effective amount of DHA comprises between 500 mg and 900 mg.

9. The method as defined in claim 6, wherein said amount of EPA and said amount of DHA comprises a 3:1 weight ratio.

10. A method for treating dry eye and improving the quality of the meibum composition of inflamed or dysfunctional meibomian glands of a mammal, comprising the steps of:
    administering a composition consisting essentially of an effective amount of omega-3 fatty acids on a daily dosage basis to said mammal having inflamed or dysfunctional meibomian glands, wherein said amount of omega-3 fatty acids comprises eicosapentaenoic acid (EPA) in an amount greater than 600 mg and in the re-esterified triglyceride form and docosahexaenoic acid (DHA) in an amount greater than 500 mg and in the re-esterified triglyceride form; and wherein said composition is devoid of omega-6 fatty acids;
    increasing levels of anti-inflammatory omega-3's in the meibum composition of said treated meibomian glands of said mammal; and
    decreasing levels of inflammatory omega-6's in the meibum composition of said treated meibomian glands.

11. The method as defined in claim 10, further comprising the steps of taking a baseline measurement of tear break up time of said mammal prior to administering said composition and taking a second measurement of tear break up time of said mammal after administration of said composition to evaluate an improvement of tear break up time of said mammal as compared to said corresponding baseline measurement.

12. The method as defined in claim 10, further comprising the steps of taking a baseline measurement of tear osmolarity of said mammal prior to administering said composition and taking a second measurement of tear osmolarity of said mammal after administration of said composition to evaluate a reduction of tear osmolarity of said mammal as compared to said corresponding baseline measurement.

13. The method as defined in claim 10, further comprising the steps of taking a baseline measurement of the quality of tears of said mammal prior to administering said composition and taking a second measurement of the quality of tears of said mammal after administration of said composition to evaluate an improvement in the quality of tears of said mammal as compared to said corresponding baseline measurement.

14. The method as defined in claim 10, wherein said amount of EPA comprises between 600 mg and 2,500 mg.

15. The method as defined in claim 10, wherein said amount of DHA comprises between 500 mg and 900 mg.

16. The method as defined in claim 10, wherein said amount of EPA and said amount of DHA comprises a 3:1 weight ratio.

17. A method for treating dry eye and improving the quality of the meibum composition of inflamed or dysfunctional meibomian glands of a mammal, comprising the steps of:
    taking a baseline measurement of tear quality of said mammal;
    administering a composition consisting essentially of an effective amount of omega-3 fatty acids on a daily dosage basis to said mammal having inflamed or dysfunctional meibomian glands, wherein said amount of omega-3 fatty acids comprises eicosapentaenoic acid (EPA) in an amount between 600 mg and 2,500 mg and in the re-esterified triglyceride form and docosahexaenoic acid (DHA) in an amount between 500 mg and 900 mg and in the re-esterified triglyceride form; and wherein said composition is devoid of omega-6 fatty acids;
    increasing levels of anti-inflammatory omega-3's in the meibum composition of said treated meibomian glands of said mammal; and
    decreasing levels of inflammatory omega-6's in the meibum composition of said treated meibomian glands.

18. The method as defined in claim 17, further comprising the step of taking a second measurement of tear quality of said mammal after administration of said composition to evaluate an improvement of tear quality of said mammal as compared to said corresponding baseline measurement.

19. The method as defined in claim 17, further comprising the steps of taking a baseline measurement of tear break up time of said mammal prior to administering said composition and taking a second measurement of tear break up time of said mammal after administration of said composition to evaluate an improvement of tear break up time of said mammal as compared to said corresponding baseline measurement.

20. The method as defined in claim 17, further comprising the steps of taking a baseline measurement of tear osmolarity of said mammal prior to administering said composition and taking a second measurement of tear osmolarity of said mammal after administration of said composition to evaluate a reduction of tear osmolarity of said mammal as compared to said corresponding baseline measurement.

* * * * *